(12) United States Patent
Kraus et al.

(10) Patent No.: US 8,708,488 B2
(45) Date of Patent: Apr. 29, 2014

(54) EYE SURGERY SYSTEM AND METHODS OF PREPARING AND PERFORMING AN EYE SURGERY

(75) Inventors: Martin Kraus, Huettlingen (DE); Christoph Kuebler, Oberkochen (DE); Delbert Peter Andrews, Oberkochen (DE); Mark Lansu, Leverkusen (DE); Thomas Schuhrke, Munich (DE); Anja Seiwert, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 72 days.

(21) Appl. No.: 13/055,233

(22) PCT Filed: Jul. 24, 2009

(86) PCT No.: PCT/EP2009/005397
§ 371 (c)(1),
(2), (4) Date: Jan. 21, 2011

(87) PCT Pub. No.: WO2010/009897
PCT Pub. Date: Jan. 28, 2010

(65) Prior Publication Data
US 2011/0122365 A1 May 26, 2011

(30) Foreign Application Priority Data
Jul. 24, 2008 (DE) .......................... 10 2008 034 490

(51) Int. Cl.
*A61B 3/14* (2006.01)
*A61B 3/00* (2006.01)
(52) U.S. Cl.
CPC ........................................ *A61B 3/14* (2013.01)
USPC ......................................... 351/206; 351/246
(58) Field of Classification Search
USPC .................................................. 351/206, 246
See application file for complete search history.

(56) References Cited

U.S. PATENT DOCUMENTS

| 5,054,907 A | 10/1991 | Sklar et al. |
| 5,349,398 A | 9/1994 | Koester |
| 5,493,109 A | 2/1996 | Wei et al. |

(Continued)

FOREIGN PATENT DOCUMENTS

| CN | 1650148 A | 8/2005 |
| DE | 102004055683 A1 | 5/2006 |

(Continued)

OTHER PUBLICATIONS

International Search Report for corresponding PCT/EP2009/005397 mailed Oct. 28, 2009.

(Continued)

*Primary Examiner* — Jack Dinh
(74) *Attorney, Agent, or Firm* — Patent Portfolio Builders PLLC

(57) ABSTRACT

A method for carrying out eye surgery comprises a comparison of images recorded before surgery with images recorded during surgery in order to generate a marker which represents a target orientation of an intraocular lens or a difference between a current orientation and the target orientation of the intraocular lens. An eye surgery system respectively comprises an imaging system which is used during a surgery and has a camera, and a diagnostic system which is used before surgery and which also has a camera. The imaging system used during surgery comprises an image processing device in order to perform a computation based on the recorded images, and in order to determine a respective orientation value, from which a representation of a marker representing the target orientation of the intraocular lens is obtained.

23 Claims, 5 Drawing Sheets

(56) References Cited

U.S. PATENT DOCUMENTS

Figure 1:
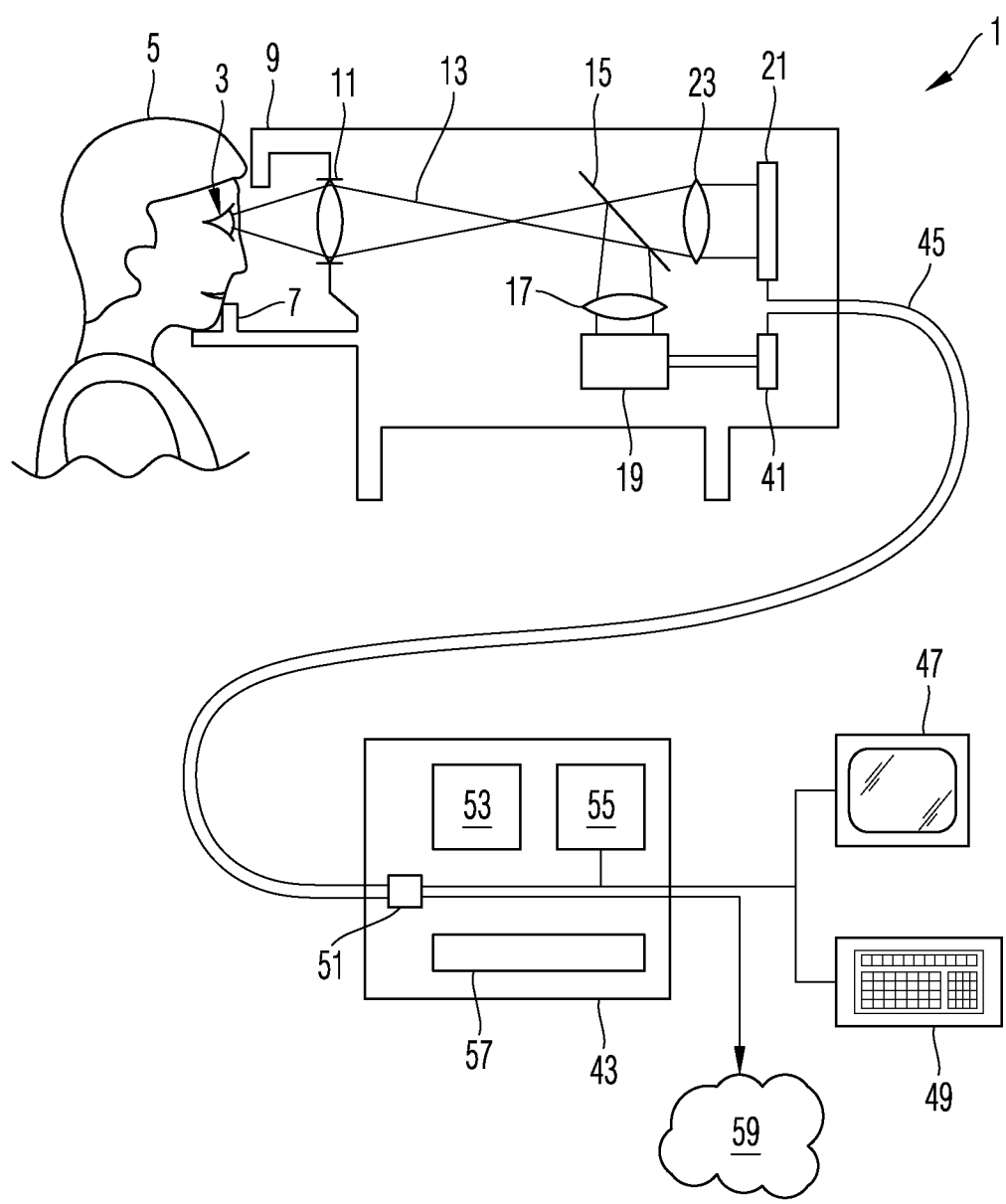

| | | |
|---|---|---|
| 6,004,314 A | 12/1999 | Wei et al. |
| 2003/0223037 A1 | 12/2003 | Cherynyak |
| 2005/0241653 A1 | 11/2005 | Van Heugten et al. |
| 2005/0243276 A1 | 11/2005 | Van Heugten et al. |
| 2006/0247659 A1 | 11/2006 | Moeller et al. |

FOREIGN PATENT DOCUMENTS

| | | |
|---|---|---|
| DE | 102005031496 | 1/2007 |
| EP | 1316287 A2 | 6/2003 |
| JP | 2005-528600 A | 9/2005 |
| JP | 2006-136714 A | 6/2006 |
| WO | 01/78584 A | 10/2001 |
| WO | 03/102498 A1 | 12/2003 |

OTHER PUBLICATIONS

Chinese Office Action in corresponding Chinese Application No. 200980137127.5 issued Oct. 9, 2012.

Chinese Office Action in corresponding Chinese Application No. 200980137127.5 issued Jul. 23, 2013.

Japanese Office Action in corresponding Japanese Application No. 2011-519088 mailed Jul. 30, 2013.

EYE SURGERY SYSTEM AND METHODS OF PREPARING AND PERFORMING AN EYE SURGERY

FIELD OF THE INVENTION

The present invention relates to an eye surgery system, a method of preparing an eye surgery and a method of performing an eye surgery.

BRIEF DESCRIPTION OF RELATED ART

An example of an eye surgery is a cataract surgery. In a cataract surgery, a crystal lens of the human eye, in which a cataract has developed, is replaced by a synthetic lens (IOL, Intra Ocular Lens). This surgery is a microsurgical intervention which is carried out by a surgeon typically using optical devices, such as, for example, a surgical microscope. For this, the surgical operator introduces an incision into the sclera or cornea, in order to introduce within the inner rim of the iris, which has been widened medicinally and without injury thereof, an opening into the capsular bag. Through this incision, the body's crystal lens is firstly removed by suction, for example after ultrasound fragmentation, and secondly the synthetic lens is inserted.

The optical characteristics of the synthetic lens are determined before the surgery, and the synthetic lens is either produced by based on the determined optical data, or it is selected from a stock of synthetic lenses based on the determined optical data. The determining of the optical data of the synthetic lens takes place on the basis of an eye examination in which characteristic data of the eye to be operated on, such as, for example, the curvature of the front surface of the cornea, the length of the eye and other factors are determined. From the geometric data of the eye which is to be operated on, the optical data of the synthetic lens are then determined so that the natural vision of the eye exists after the insertion of the synthetic lens and the patient preferably does not have to wear spectacles or only has to wear spectacles of low power to correct defective vision. For this, it is occasionally also desirable to insert a synthetic lens having an astigmatic property into an eye which is to be operated on. The astigmatic property can be characterized for example by two different refractive powers in directions which are orthogonal to each other, and an orientation of an axis with respect to, for example, the horizontal direction or the horizontal axis of the head.

From DE 10 2004 055 683 A1 there are known a device and a method to assist a surgeon in inserting an astigmatic synthetic lens into the eye of a patient.

It has been found that the conventionally practised methods together with the developed assisting equipment do not always achieve the desired success.

SUMMARY OF THE INVENTION

It is an object of the present invention to improve conventional eye surgery systems and methods of preparing and carrying out eye surgery. It is likewise an object of the invention to propose an eye surgery system which could be helpful in inserting an astigmatic synthetic lens, and it is also an object of the present invention to provide a method for preparing an eye surgery and a method of performing an eye surgery, which could likewise be helpful in inserting an astigmatic synthetic lens.

Embodiments of the invention provide an eye surgery system including a display device configured to generate a representation of a marker which can be perceived by a surgeon and can in particular assist him in orienting a synthetic lens which is inserted into an eye relative to the eye.

According to an embodiment of the present invention, a display device of an eye surgery system generates a representation of an eye and a representation of a marker, wherein the marker is represented based on an orientation value which has been determined by an image processing device. The representation can be produced by the display device such that the representation of the eye and the representation of the marker are superimposed with each other. The image processing device is configured to determine the orientation value based on a first image and a second image. The determining may include in particular a calculation involving the two images, such as, for example, a comparison of the first image with the second image. The first image was recorded at an earlier moment than the second image. In particular, the recording of the second image may take place immediately before the representation of the eye together with the marker, whereas the recording of the first image may take place half an hour or several hours or several days before the recording of the second image. Accordingly, the eye surgery system may comprise an image memory for storing the first image. The eye surgery system may, however, also comprise an image memory storing the second image.

According to an embodiment of the invention, an eye surgery system includes an imaging system which in practice can be similar to, for example, a conventional surgical microscope, wherein the imaging system comprises: a data memory for an orientation value, an image memory for a first image of an eye under surgery and recorded prior to the surgery, a camera for recording a second image of the eye under surgery during the surgery, an image processing device which is configured to determine an orientation value based on the first image and the second image, and a display device for generating a representation of the eye and a representation of a marker based on the determined orientation value.

According to a further embodiment of an eye surgery system, an imaging system includes a stand for mounting a camera at a distance from the eye under surgery, wherein the stand includes a plurality of joints which permit a displacement of the camera in three spatial directions orthogonal to each other. Hereby, the camera which records images of the eye under surgery can be positioned by the surgeon or an assistant so that it is advantageous for the surgeon and corresponds to the position of the patient.

The imaging system may include, for example, a surgical microscope which may comprise, for example one, two or more objective lenses and one or more individual oculars or pairs of oculars. The camera may be arranged in a beam path of the surgical microscope and may, for example, receive light having traversed an objective lens of the microscope for generating an image of the eye.

According to an embodiment, the display device may include an image projector for projecting a representation of the marker into the beam path towards the ocular.

According to an embodiment of the invention, the display device may comprise a head-mounted device ("head-mounted display") and/or a monitor which is carried on a bracket or a stand.

According to an embodiment of the invention, the display device may comprise an interface for receiving the first image, i.e. the image which was recorded some time before the second image, so that an image processing device can process this received first image.

According to an embodiment of the present invention, the eye surgery system includes a diagnostic system which may be separate from the imaging system. The diagnostic system includes a camera to record the first image of the eye which is to be operated on, and an interface for outputting the first image in a format which is in particular suitable for immediate input to the input device and for processing by the image processing device.

According to an exemplary embodiment herein, the diagnostic system is further configured to measure geometry parameters of the eye which is to be operated on and to provide the corresponding measured data in such a way that the optical data of a synthetic lens can be calculated which is suited for insertion into the eye which is examined by the diagnostic system. This calculation can be based on formulas which have been obtained empirically, wherein the calculations based on such formula can in particular be performed in a computer-assisted manner. It is also possible that the diagnostic system directly outputs the optical data of the synthetic lens. These data preferably include an orientation value which represents a desired orientation of the synthetic lens relative to the eye.

According to an embodiment of the present invention, a method is provided for preparing an eye surgery, which includes: recording a first image of an eye of a patient, recording a second image of the eye, providing a representation of the eye, determining an orientation relative to the representation of the eye based on the recorded first image and the recorded second image, and generating a representation of a marker based on the determined orientation and superimposed with the representation of the eye.

Herein, the marker may indicate an orientation according to which a synthetic lens which is to be subsequently inserted into the eye is to be oriented, in order to achieve good eyesight with the eye having the inserted synthetic lens. As the orientation is determined inter alia based on the first image of the eye which was recorded before recording of the second image, the synthetic lens can be oriented subsequently with a relatively high degree of accuracy. It is in particular possible that, when the second image is recorded, the eye is rotated within the eye socket of the patient relative to its normal position, such that a determination of the orientation based only on the second image would result in a non-optimum orientation.

For example, such rotation can be caused by a manipulation of the eye. Further, such rotation can be caused by an effect called "cyclotorsion", according to which a person's eye can rotate in the eye socket by up to 10° when the person transfers from a sitting position into a lying position. The extent and amount of this rotation are different, however, from patient to patient, so that they can be predicted with only difficulty. In particular, this effect is of importance if the measurement of the eye performed prior to the surgery takes place when the patient's head is in an upright position, and if the recording of the second image and the subsequent orientation of the synthetic lens takes place when the head is in a lying position.

By determining the orientation based on the first image and the second image, it is possible to compensate for a rotation of the eye in the eye socket when the second image is recorded relative to the recording of the first image. In particular, it is possible to determine the orientation such that it corresponds to a desired orientation relative to the eye when the first image was recorded.

The determining of the orientation based on the first image and the second image may in particular involve an image comparison, which is directed to structures of the sclera of the eye, such as, for example, structures of blood vessels. Often, structures of the iris of the eye are not available for such a comparison, since the iris has usually been medicinally widened at the time of recording of the second image, so that it is visible only to a very small extent in the second image. However, it is possible to locate other structures of the eye which are visible in the sclera, such as blood vessels, with a sufficient quality in the images, such that an image comparison based on these located structures allows the calculation of the orientation of the eye in the second image relative to the orientation of the eye in the first image.

It is envisaged to use a camera having a high resolution to record the first image and to record the second image in order to detect the structures in the sclera with sufficient accuracy. For example, the cameras for this purpose may include an array of image elements or pixels, the number of which is greater than, for example, 960×720=691,200 pixels or greater than, for example, 1,280×720=921,600 pixels or greater than 2 million pixels. In particular, the camera of the diagnostic system may include a greater number of pixels than the camera of the imaging system.

According to specific embodiments, an optical filter can be provided in a beam path towards the camera which records the first image and in a beam path towards a camera which record the second image, which filter selectively affects the spectrum of the light used for the generation of the images. For example, the filter may be an infrared filter which only allows infrared light, i.e. light having, for example, a wavelength greater than 800 nm, or the filter may be a band-pass filter, which is adapted to an emission spectrum of a fluorescent dye. Likewise, the camera can be an infrared camera or another camera which is selectively sensitive to particular wavelength ranges and which has a corresponding filter already integrated with the camera.

The method explained for preparation of the eye surgery as illustrated above is free of steps breaking the integrity of the human body of the patient, so that his method does not necessarily have to be carried out by a surgeon, but rather can also be carried out by an assistant who prepares the patient for the surgery performed by the surgeon.

According to a further embodiment of the present invention, a method is provided for carrying out an eye surgery which may, for example, also include the removal of the crystal lens from the eye. According to an embodiment, this method also includes the insertion of a synthetic lens into the eye and an orientation of the synthetic lens relative to the eye.

According to a further embodiment of the invention, a marker can be applied to the eye, for example in a region of the sclera, which marker is visible in the recorded first image and which remains on the eye at least for a limited period of time until the second image is recorded. Such marker can be used in the image comparison between the first image and the second image in order to determine the relative orientation of the eye in the two images. This can be helpful in particular when natural structures, such as, for example, blood vessels in the sclera, can not be detected with high contrast in the images. The marker can be applied to the sclera as a groove or the like using, for example, a knife. In addition, it is possible to apply the marker on the eye using a dye, wherein the dye can be biodegradable such that it is no longer visible after a few hours or days, for example.

EXEMPLARY EMBODIMENTS

Figure 2:
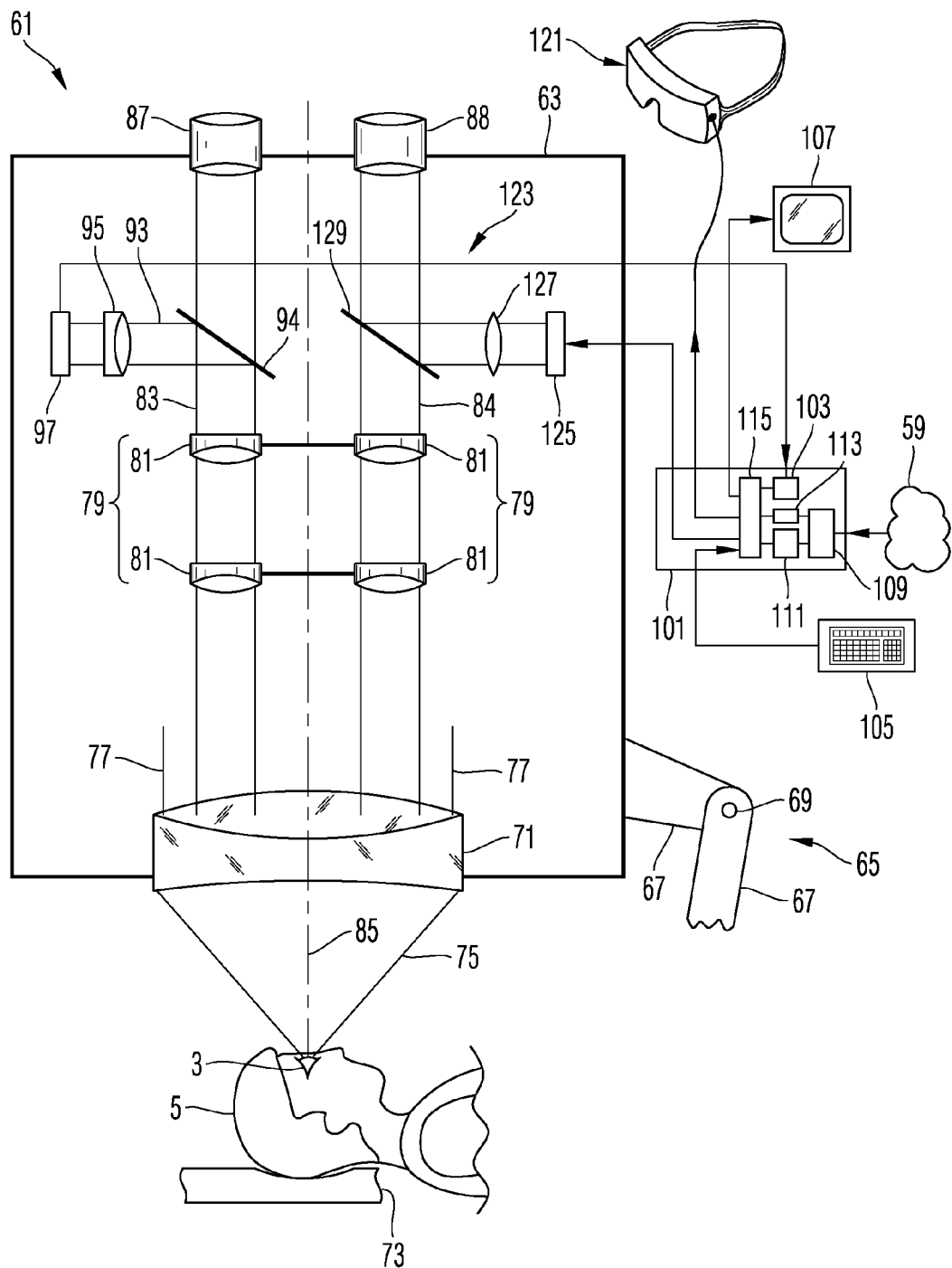
Figure 3:
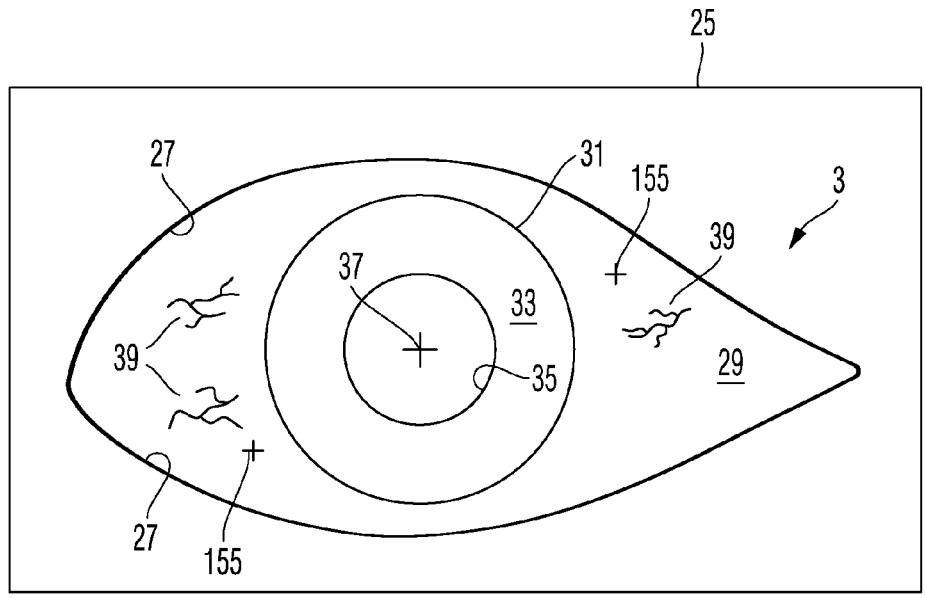
Figure 4:
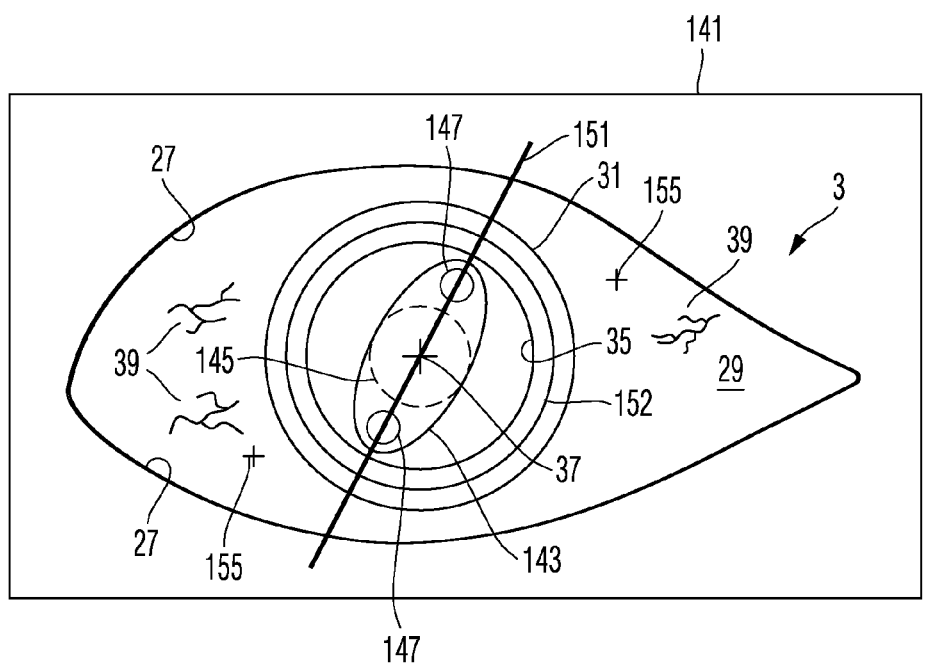
Figure 5:
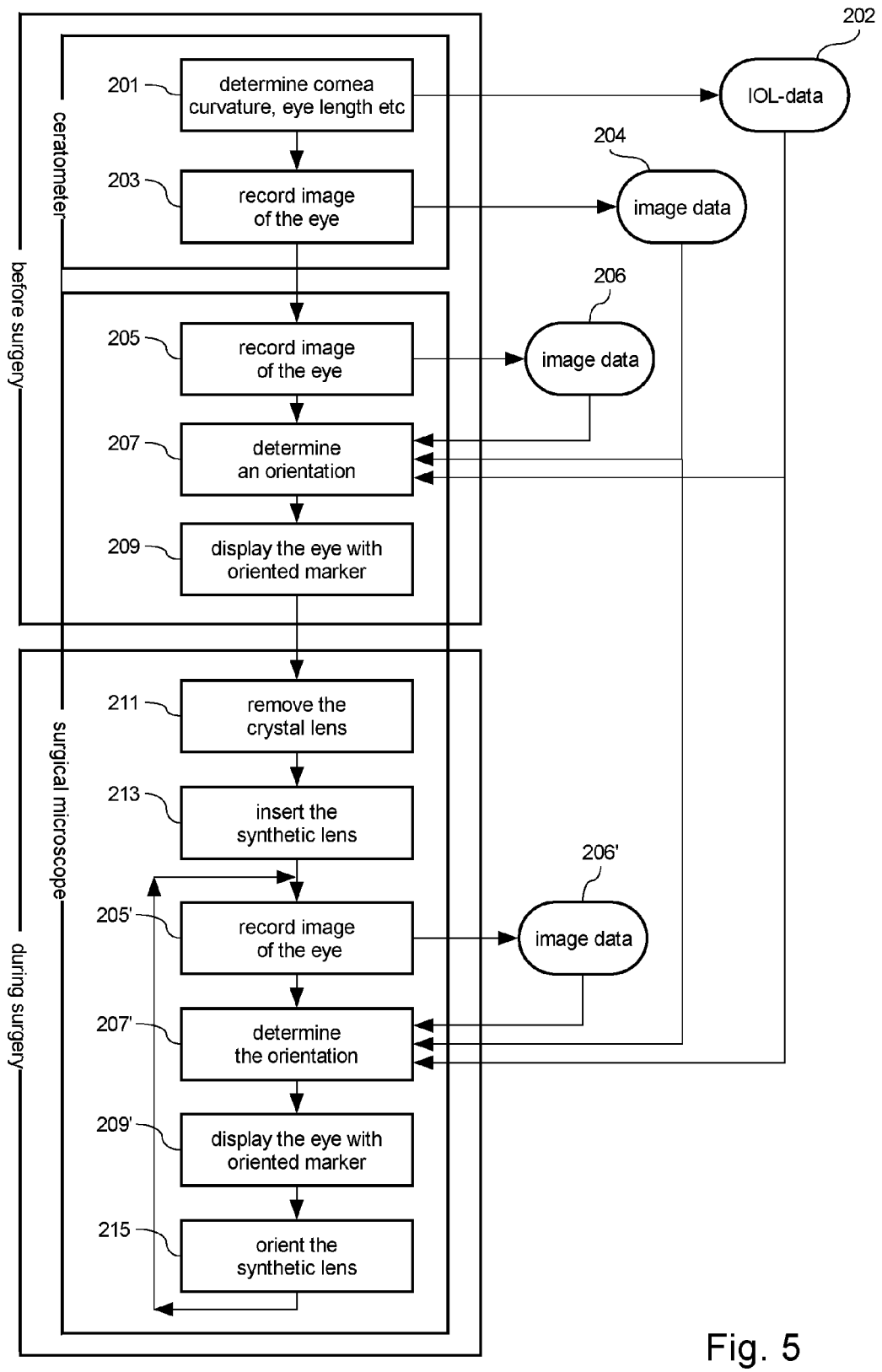
Figure 6:
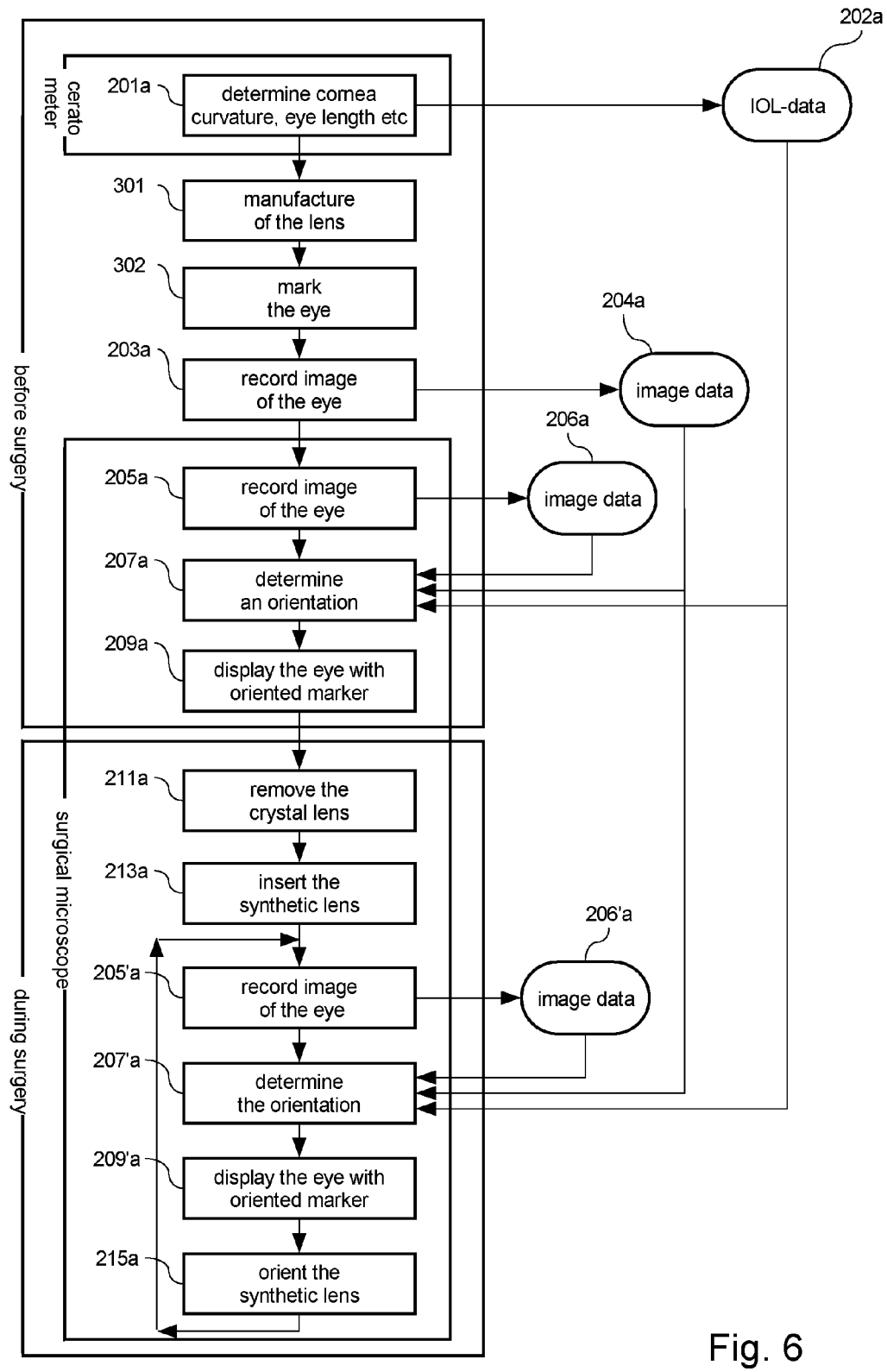

Embodiments of the invention are explained in further detail below with the aid of drawings, in which:

FIG. 1 is a diagrammatic illustration of a diagnostic system of an eye surgery system according to an embodiment of the invention, FIG. 2 is a schematic illustration of an imaging system of the eye surgery system, the diagnostic system of which is shown in FIG. 1, FIG. 3 is a schematic illustration of a first image of a patient's eye as recorded with a camera of the diagnostic system of FIG. 1, FIG. 4 is a schematic illustration of a second image of the patient's eye as recorded with a camera of the imaging system of FIG. 2, FIG. 5 a flow chart for illustrating methods according to embodiments of the invention, and FIG. 6 a flow chart for illustrating methods according to further embodiments of the invention.

An eye surgery system according to an embodiment of the invention includes a diagnostic system which will be illustrated below with reference to FIG. 1, and an imaging system which will be illustrated below with reference to FIG. 2.

A diagnostic system 1 serves to measure an eye 3 of a patient 5. For this, the diagnostic system 1 comprises a rest 7 for a chin of the patient and an abutting support 9 for a forehead of the patient, so that his eye 3 is arranged opposite to input optics 11 of the diagnostic system 1. A measuring beam path 13 is reflected at a semi-transparent mirror 15 and enters via intermediate optics 17 into a schematically represented measurement module 19 of the diagnostic system 1. The measurement module 19 serves to obtain geometry data of the eye, such as, for example curvatures of the cornea of the eye and a length of the eyeball. In this respect, the diagnostic system corresponds to a conventional diagnostic system, such as, for example, a ceratometer; examples of this are known for example from U.S. Pat. No. 5,054,907 and U.S. Pat. No. 5,349,398, or an OCT (optical coherence tomography) system; examples of this are known for example from U.S. Pat. No. 5,493,109 or U.S. Pat. No. 6,004,314. An example of a diagnostic system is a system which is marketed under the name IOL Master by Carl Zeiss Meditec, Jena, Germany.

Furthermore, according to the illustrated embodiment of the invention, the diagnostic system comprises a high-resolution camera 21 having, for example, 1,280×720 pixels to which light having traversed the semi-transparent mirror 15 is supplied via camera optics 23. A first image of the eye 3 can be recorded by the high-resolution camera 21. An example of such an image is illustrated schematically in FIG. 3. The image 25 shown there represents eyelids 27, sclera 29, an outer rim 31 of an iris 33, an inner rim 35 of the iris 33 and a center 37 of the pupil. Further, blood vessels 39 can be seen in the image 25.

The measurement data obtained with the measurement module of the diagnostic system 1 are transferred to an intermediate memory 41 and can be read from there into a control system 43 via, for example, a data line 45. The control system 43 may be provided by, for example, a personal computer to which output devices, such as, for example, a monitor 47, and input devices, such as, for example, a keyboard 49, are connected. The controller 43 receives the measurement data via an interface 51, processes them further and may store results of the measurement of the eye 3 in a data memory 53. Similarly, one or more sets of image data obtained by the camera 21 can be inputted via, for example, the data line 45 and the interface 51 into the controller 43, can be further processed there and stored as image data in an image memory 55. The measurement data from the memory 53 and the image data from the memory 55 can then be written to, for example, a compact disc arranged in a drive 57, or transferred to a network 59. The measurement data include in particular optical data for a synthetic eye lens including an astigmatic characteristics and hence in particular two refractive powers and an orientation.

The imaging system 61 shown in FIG. 2 includes a housing body 63 which is carried by a stand 65, only a portion of which is schematically shown in FIG. 2, and which comprises plural stand members 67 and joints 69 in order to position an objective lens 71 of the imaging system 61 at a distance from the eye 3 of the patient 5, whose head 5 rests lying on a pillow 73 for a cataract surgery to be carried out. An object side imaging beam bundle 75 originating from an object plane of the objective 71 is transformed by the objective lens 71 into an image side beam bundle 77. A pair of zoom systems 79 having plural lenses 81 pick up two partial beam bundles 83 and 84 from the beam bundle 77, wherein the beam bundles 83 and 84 are parallel and symmetric to an optical axis 85 of the imaging system and are supplied to oculars 87 and 88, respectively, into which a surgeon can look with his left and right eyes in order to observe an image of the eye 3.

The imaging system 61 further includes a semi-transparent mirror 91 which is located in the partial beam bundle 83 for directing a beam bundle 93 to a camera chip 97 via adapter optics 95, such that an image of the eye 3 is produced on the camera chip 97. Images recorded by the camera chip 97 are read by a controller 101 of the imaging system 61 and stored in an image memory 103.

Again, the controller 101 can be a personal computer to which input devices, such as, for example, a keyboard 105, and output devices, such as, for example, a monitor 107, are connected.

The controller 101 further comprises an interface 109 which is connected, for example, to the network 59, for receiving at least a portion of the data generated by the diagnostic system 1. The interface 103 can likewise be connected to a data carrier reader, for reading these data from, for example, a compact disc.

The controller 101 includes an image memory 111 for storing the first image 25 recorded by the diagnostic system 1, for example.

The controller 101 further includes a data memory 113 for storing the determined target orientation of the synthetic lens. A computing and image processing device 115 of the controller 101, which may be implemented in the controller 101 as software, calculates, based on the first image of the eye stored in the memory 111, the second image of the eye stored in the memory 103 and the target orientation stored in the memory 103 a further image which is displayed on the monitor 107. In addition to the monitor 107, this further image can also be displayed by a head-mounted display 121. Furthermore, the illustrated embodiment of the imaging system 61 comprises a projector 123 including a display device 125, such as, for example, an LCD display, projection optics 127 and a semi-transparent mirror 129. The semi-transparent mirror 129 is arranged in the partial beam bundle 84 and projects a pattern displayed by the display device 125 and projected by the optics 127 into the partial beam bundle 84 such that it is perceived in superposition with the image of the eye 3 when looking into the ocular 26.

FIG. 4 shows a schematic representation 141 as it is displayed by the computing and image processing device 115 on the monitor 107. In the representation, a toric intraocular lens 143 is already introduced into the capsular bag of the eye 3. Due to its astigmatic optical property, the toric intraocular lens 143 is to be oriented correctly in the capsular bag of the eye 3. In this surgery, the pupil is medicinally widened, and this is the reason why a distance between the inner periphery 35 of the iris and the outer periphery 31 of the iris is reduced as compared to the illustration of FIG. 3.

The intraocular lens 143 comprises a central lens portion 145 and opposite extended peripheral portions including haptics 147, respectively. The haptics 147 can be perceived in the illustration clearly as shape features of the intraocular lens and can serve as a markers. However, it is also possible that additional markers, such as, for example, lines, are applied to on the lens 143 in order to serve as an orientation aid.

In the representation 141, the elements of the eye such as lids 27 and iris 31, 35 and the intraocular lens 143 are illustrated so that they correspond to the image of the eye recorded by the camera 97. A line or marker 151 is shown in the representation 141 in superimposition with these elements of the eye, wherein the line or marker 151, extends through the centre 37 of the pupil and is, in the representation 141, oriented such that the intraocular lens 143 is correctly oriented in the eye according to its target orientation, if the centers of the haptics 147 coincide with the line 151.

The representation of the marker 151 is generated by the computing and image processing unit 115 as follows:

The computing and image processing unit 115 determines the inner periphery 35 of the iris in the image recorded by the camera 97 and stored in the image memory 103, in order to determine the position of the center 37 in the representation 141 and to represent the center 37 as a cross or other marker. In addition, a circle 152 can be displayed around the centre 37 in order to be able to verify a correct position of the markings and hence a correct functioning of the system, wherein the circle extends, for example, between the inner periphery 35 and the outer periphery 31 of the iris. In addition, the image processing unit 115 compares the images stored in the memories 103 and 111 with each other with regard to structures of the cornea, such as, for example, the blood vessels 39. From this comparison, the computing unit 115 calculates a relative rotation of the eyes shown in the images. For example, the eye imaged by the camera 97 can be rotated relative to the image of the eye recorded by the camera 21 of the diagnostic system 1 due to cyclotorsion. The computing and image processing unit 115 then determines, based on the target orientation of the intraocular lens stored in the memory 113 and based on the rotation obtained from the image comparison, a current orientation which the intraocular lens 143 should have in the representation 141 in order to be correctly oriented. This current orientation is illustrated by the straight line 151 as a marker in the representation 141. The surgeon is then able to align the intraocular lens according to the marker 151.

The explained process for calculating the marker 151 can be repeated by the display device 61 and carried out based on the continuously updated current images recorded by the camera 97, such that the representation of the marker 151 is updated after a short delay of, for example, 300 ms or nearly in real time.

While both the representation of the marker and the representation of the elements of the eye are displayed on the output devices monitor 107 and head-mounted display 121, it is sufficient if the display device 125 only shows the marker 151, since the superposition with the elements of the eye is produced by the semi-transparent mirror 129 in the beam path of the ocular 88.

It is further possible to apply two or more markers 155 to the sclera 29 of the eye before recording the first image with the camera 21 of the diagnostic system 1. The markers 151 can be formed, for example, by an ink or a specifically produced small lesion in the sclera. These markers 155, just as the structures of the blood vessels 39, are visible in the recorded images and can be used in the image processing to determine the relative rotation of the images more easily and with greater reliability.

In the illustration of FIG. 1, the imaging system 61 is a surgical microscope comprising two ocular beam paths. However, it is also possible to use a less complicated imaging system which does not have oculars, wherein the displaying must then be performed via a monitor or a head-mounted display.

Embodiments of the method of preparing an eye surgery and of the method of performing an eye surgery are summarized with reference to the flow chart shown in FIG. 5. By using a diagnostic system which can have functions of a conventional ceratometer or by using an OCT system, IOL data 202, i.e. optical data of a synthetic intraocular lens are determined in a step 201 based on measured data obtained from the eye which is to be operated on, such as, for example, curvature of the cornea and eye length. Image data 204 of the eye are recorded by a camera integrated with the diagnostic system in a step 203, such that an orientation of the image data and the target orientation of the intraocular lens contained in the IOL data are obtained relative to a common reference orientation, which can be. for example, the vertical direction. The patient's head can be oriented upright during the examination with the diagnostic system.

Based on the IOL data 202, an order for the manufacture of an intraocular lens is placed, or a matching intraocular lens is selected from a stock of such lenses.

The patient is then positioned with his eye in front of the display device, which assists in performing the surgery. The display device can be a surgical microscope, and the patient's head can be arranged recumbent or horizontally. Firstly, an assistant checks the position of the patient and carries out necessary adjustments of the display device, which may also include the correct displaying of the marker which indicates the correct orientation of the intraocular lens in the eye of the patient. For this purpose, image data 206 are obtained with a camera of the display system in a step 205. The image data undergo a calculation together with the image data 204 and the target orientation included in the IOL data 202 in a step 207, in order to determine an orientation of the intraocular lens in the image recorded in step 205. Both elements of the eye which correspond to the image of the eye recorded in step 205 and also a marker which represents the target orientation of the intraocular lens in the eye are represented in a step 209.

The steps 201, 203, 205, 207 and 209 can be carried out by an assistant who is different from the surgical operator or surgeon who carries out the microsurgical intervention.

Subsequently, the surgeon carries out a step 211 in order to remove the crystal lens from the eye of the patient. Thereafter, the synthetic eye lens is inserted into the eye in a step 213. Subsequent steps 205', 207' and 209' follow, which correspond to the steps 205, 207 and 209 illustrated above, in order to achieve an updated representation of a marker which represents the target orientation of the synthetic eye lens. For this purpose, a computation is performed based on updated image data 206' obtained in step 205', the image data 203 and the IOL data 202 in a step 207', and the result of this computation is displayed in a step 209', wherein the surgeon detects from the representation generated in step 209' a need for correction for the orientation of the lens and, if applicable, corrects the orientation of the synthetic eye lens in a step 215. The steps 205', 207', 209' and 215 can be repeated until the surgeon is satisfied with the result of the orientation of the synthetic eye lens.

Unlike the steps 201, 203, 205, 207 and 209 performed before the surgery and which can be carried out by an assistant, the steps 211, 213, 205', 207', 209' and 215 are designated as intra-surgery steps which are carried out by a surgical operator or surgeon.

Further embodiments of the method of preparing an eye surgery and of the method of performing an eye surgery are illustrated with reference to the flow chart shown in FIG. 6. Herein, reference numerals, which are similar to reference numerals used in FIG. 5, designate steps of the embodiments illustrated with reference to FIG. 6 which correspond to those of the embodiments illustrated with reference FIG. 5. These similar reference numerals are identical in the numbers and differ only by the additional letter "a". In order to avoid a redundant description hereinbelow, reference is made to the illustration of the corresponding steps in the description of FIG. 5 for the description of the steps designated by similar reference numbers.

In a manner similar to the embodiment illustrated with reference to FIG. 5, data for the required intraocular lens, i.e. IOL data 202a are determined in a step 201a by measuring the eye. The intraocular lens is produced based on the IOL data 202a in a step 301. Here, the production can be carried out by a manufacturer who is specialized in such manufacture and to which the IOL data 202 are sent via a telecommunications medium, such as facsimile or email, and which eventually sends the intraocular lens which has been manufactured to the doctor, hospital or patient, so that it is provided there ready for implantation.

A marker is applied to the eye which is to be operated on in a step 302. The marker can be applied on the eye in any desired manner, as long as it can be subsequently observed in recorded images. Examples of the application of markers on the eye include: applying a depression or groove using a hard object, applying an indentation or depression or the like by a knife or the like, applying a dye, such as an ink, on the sclera of the eye using a pen or a spraying device, and others.

After the marker is applied to the eye, in a step 203a a first image of the eye is recorded, which provides image data 204a, from which subsequently the orientation of the eye and a target orientation of the intraocular lens is obtained relative to a reference orientation, as was explained previously with reference to FIG. 5.

The applying of the marker in step 302 takes place in the embodiment illustrated with reference to FIG. 6 after the manufacture of the lens and immediately before the recording of the image in step 203a. However, it is possible to already carry out the marking of the eye before the manufacturing of the lens (step 301) and after the determining of the IOL data (step 201a), and it is further possible to carry out the marking of the eye (step 302) even before the determining of the IOL data (step 201a). The moment of carrying out step 302a depends inter alia on how long the marking which is applied to the eye is visible. Certain markers, such as for example markings by ink or by depressions produced by pressing, fade over time or diminish. The manufacturing of the lens can take a few hours or a few days, and accordingly the marking on the eye is to be carried out before or after the manufacturing of the lens, depending on the duration of visibility of the marker.

After the first image of the eye is recorded in step 203a, subsequent steps 205a to 215a are carried out in a similar manner as the steps of the embodiment illustrated with reference to FIG. 5, and they are not illustrated separately here in order to avoid repetitions.

In the embodiments illustrated above, a representation of the eye which is to be operated on is generated by the eye surgery system, wherein the representation is superimposed with a representation of a marker which indicates the target orientation of the intraocular lens which is to be inserted to the surgical operator.

Alternatively or in addition to this, it is likewise possible to integrate a wave front sensor into the imaging system. Examples of wave front sensors are known from US 2005/0241653 A1, US 2005/0243276 A1 or DE 10 2005 031 496 B4, the full disclosures of which are incorporated by reference into the present application. In addition, it is possible to integrate a ceratometer into a surgical microscope or to connect a ceratometer to a surgical microscope. By means of such wavefront sensor, an ametropia of the eye under surgery, in particular with regard to an amount and an orientation of an astigmatism, can be determined during the surgery. Likewise, with a ceratometer, or with a similar system such as for example a ceratoscope or an ophthalmometer, the ametropia, in particular with regard to amount and orientation of an astigmatism, of the eye under surgery can be determined during the surgery.

Therefore, it is in particular possible to also determine an orientation of the intraocular lens deviating from the target orientation, and to represent such orientation for the surgeon in a suitable manner. This can take place for example by displaying a marker or an indicator in the image of the eye which is observed by the surgeon during the surgery. This indicator may include a numerical value, such as for instance "+7", which can denote a meaning such as "rotate the lens clockwise by 7°", whereas an indicator of "−3" may have a meaning such as "rotate anti-clockwise by 3°". In addition, a direction of the rotation of the intraocular lens which is to be carried out can be indicated by arrows or the like pointing in a clockwise or anti-clockwise direction.

According to an embodiment of the invention, a method is provided for performing an eye surgery, wherein the method includes a comparison of images recorded before the surgery with images recorded during the surgery in order to generate a marker which represents a target orientation of an intraocular lens or a difference between a current orientation and the target orientation of the intraocular lens.

Further, an eye surgery system is provided, which includes an imaging system which is used during the surgery and which comprises a camera, and a diagnostic system which is used before the surgery and which also has a camera. The imaging system used during the surgery comprises an image processing device for performing a calculation based on the recorded images and for determining a respective orientation value which forms the basis for obtaining a representation of a marker representing the target orientation of the intraocular lens.

The invention claimed is:

1. An eye surgery system including an imaging system, wherein the imaging system comprises:
   a data memory configured to store an orientation value;
   an image memory configured to store a first image of an eye under surgery recorded prior to the surgery;
   a camera configured to record a second image of the eye under surgery during the surgery;
   an image processing device configured to determine an orientation value based on the first and second images; and
   a display device configured to generate a representation of a marker based on the determined orientation value.

2. The eye surgery system according to claim 1, wherein the imaging system further comprises a stand configured to mount the camera at a distance from the eye under surgery, wherein the stand comprises a plurality of joints allowing a displacement of the first camera in three spatial directions orthogonal to each other.

3. The eye surgery system according to claim 1, wherein the imaging system comprises a surgical microscope having an imaging beam path, and wherein the camera is positioned in the imaging beam path of the surgical microscope.

4. The eye surgery system according to claim 3, wherein the display device includes an ocular positioned in the imaging beam path of the surgical microscope.

5. The eye surgery system according to claim 4, wherein the display device further includes an image projector configured to project the representation of the marker into the beam path towards the ocular.

6. The eye surgery system according to claim 1, wherein the display device comprises at least one of a head-mounted display device and a monitor.

7. The eye surgery system according to claim 1, wherein the display device comprises an interface configured to input the first image to the image memory.

8. The eye surgery system according to claim 1, further including a diagnostic system, wherein the diagnostic system comprises:
   a camera configured to record the first image of the eye under surgery prior to the surgery; and
   an interface configured to output the first image.

9. The eye surgery system according to claim 8, wherein the diagnostic system is configured to determine at least one orientation of an eye astigmatism of the eye, and wherein the diagnostic system comprises an interface configured to output an orientation value representing the determined orientation of the astigmatism.

10. The eye surgery system according to claim 9, wherein the diagnostic system determines the at least one orientation of the eye astigmatism of the eye when a head of the patient is in an upright position, and
   further wherein the surgery system inserts an astigmatic intraocular lens (IOL) into the eye when the head of the patient is in a horizontal position.

11. The eye surgery system according to claim 8, wherein the camera of the diagnostic system comprises a detector having an array of image elements, and wherein a number of the image elements of the diagnostic system is greater than or equal to a number of image elements of the detector of the camera of the imaging system.

12. A method of preparing a surgery on an eye, wherein the method comprises:
   recording a first image of an eye of a patient;
   recording a second image of the eye;
   determining an orientation based on the first recorded image and the second recorded image; and
   generating a representation of a marker based on the determined orientation.

13. The method according to claim 12, wherein the first image of the eye is recorded when a head of the patient is in an upright position.

14. The method according to claim 12, wherein the second image of the eye is recorded when the head of the patient is in a lying position.

15. The method according to claim 12, further comprising generating a representation of the eye by optically imaging the eye, and projecting the representation of the marker into the representation of the eye.

16. The method according to claim 12, further comprising generating a representation of the eye by displaying the second image.

17. The method according to claim 12, wherein the recording of the second image, the determining of the orientation and the generating of the representation of the marker are carried out repeatedly after the first image of the eye has been recorded.

18. The method according to claim 12, further comprising determining an orientation of an eye astigmatism of the eye, wherein the generating of the representation of the marker is further based on the determined orientation of the eye astigmatism.

19. The method according to claim 12, further comprising applying at least one marker on the eye before recording of the first image.

20. The method according to claim 12, further comprising measuring of optical characteristics of the eye of the patient and manufacturing an intraocular lens based on the measured optical characteristics.

21. The method according to claim 20, wherein the second image is recorded after the manufacturing of the intraocular lens.

22. A method of performing an eye surgery, wherein the method comprises
   recording a first image of an eye of a patient;
   recording a second image of the eye;
   determining an orientation based on the first recorded image and the second recorded image; and
   generating a representation of a marker based on the determined orientation; wherein the first image is recorded prior to the surgery and the second image is recorded during the surgery.

23. The method according to claim 22, further comprising orienting an intraocular lens relative to the eye based on the representation of the marker.

* * * * *